(12) United States Patent
Daly

(10) Patent No.: US 10,631,738 B2
(45) Date of Patent: Apr. 28, 2020

(54) SYSTEM FOR ANALYZING OXIMETRY DATA

(71) Applicant: Periodic Breathing Foundation, Providence, RI (US)

(72) Inventor: Robert W. Daly, Providence, RI (US)

(73) Assignee: The Periodic Breathing Foundation, LLC, Cooke Street Providence, RI (US)

( * ) Notice: Subject to any disclaimer, the term of this patent is extended or adjusted under 35 U.S.C. 154(b) by 739 days.

(21) Appl. No.: 13/956,002

(22) Filed: Jul. 31, 2013

(65) Prior Publication Data

US 2014/0039283 A1 Feb. 6, 2014

Related U.S. Application Data

(60) Provisional application No. 61/677,787, filed on Jul. 31, 2012.

(51) Int. Cl.
*A61B 5/08* (2006.01)
*A61B 5/0205* (2006.01)
(Continued)

(52) U.S. Cl.
CPC ........ *A61B 5/0205* (2013.01); *A61B 5/02405* (2013.01); *A61B 5/0816* (2013.01);
(Continued)

(58) Field of Classification Search
CPC . A61B 5/0205; A61B 5/02405; A61B 5/0816; A61B 5/4818
See application file for complete search history.

(56) References Cited

U.S. PATENT DOCUMENTS

| | | | |
|---|---|---|---|
| 4,289,142 A * | 9/1981 | Kearns | A61B 5/02455 600/529 |
| 2002/0095076 A1* | 7/2002 | Krausman | A61B 5/14552 600/323 |

(Continued)

OTHER PUBLICATIONS

Dujic et al, Central chemoreflex sensitivity and sympathetic neural outflow in elite breath-hold divers, 2008, Journal of Applied Physiology, 104(1): 205-211.*

(Continued)

*Primary Examiner* — Eric J Messersmith
(74) *Attorney, Agent, or Firm* — Barlow, Josephs & Holmes, Ltd.

(57) ABSTRACT

A method and system for the analysis of a patient's oximetry data to detect sleep-disordered breathing is provided. The system employs an algorithm to reliably detect patient arousals and correlate those with accelerated heart rate and oxygen saturation levels in a manner that detects sleep-disordered breathing via the respiratory mask. Initially a timing channel is formed based on a plethsmography signal using an optical finger sensor. Based on the pleth waveform, a respiratory wave form is prepared that represents respiration rate. An arousal mask is applied to the signal based on attenuations in the pleth signal. Once arousals are identified the time required for changes to propagate from the lungs to the blood gas is subtracted from the onset time of the arousal. As a result if the timing agrees with dropping oxygen saturation or falling arterial pH then the arousal is indicated as a chemoreflex related arousal.

16 Claims, 3 Drawing Sheets

(51) Int. Cl.
  *A61B 5/1455* (2006.01)
  *A61B 5/00* (2006.01)
  *A61B 5/024* (2006.01)

(52) U.S. Cl.
  CPC ........ *A61B 5/14551* (2013.01); *A61B 5/4818* (2013.01); *A61B 5/7278* (2013.01)

(56) References Cited

U.S. PATENT DOCUMENTS

| | | | |
|---|---|---|---|
| 2003/0163054 A1* | 8/2003 | Dekker | A61B 5/02416 600/502 |
| 2003/0187336 A1* | 10/2003 | Odagiri | A61B 5/1118 600/300 |
| 2008/0066753 A1* | 3/2008 | Martin | A61M 16/0051 128/204.23 |
| 2009/0240126 A1* | 9/2009 | Baker, Jr. | A61B 5/0205 600/324 |
| 2014/0088378 A1* | 3/2014 | Muzet | A61B 5/02125 600/301 |

OTHER PUBLICATIONS

Tipton, ACSM's Advanced Exercise Physiology, 2006, Lippincott Williams & Wilkins, p. 221.*

* cited by examiner

SYSTEM FOR ANALYZING OXIMETRY DATA

CROSS-REFERENCE TO RELATED APPLICATIONS

This application is related to and claims priority from earlier filed U.S. Provisional Patent Application No. 61/677,787, filed Jul. 31, 2012.

BACKGROUND OF THE INVENTION

The present invention relates to a method and system for the analysis of oximetry data for the detection of sleep-disordered breathing therefrom. More specifically, the present invention relates to a system that employs an algorithm to reliably detect patient arousals and correlate those with accelerated heart rate and oxygen saturation levels in a manner that detects sleep-disordered breathing via a patient's oximetry data.

Nearly one in seven people in the United States suffer from some type of chronic sleep disorder. Further, only 50% of people are estimated to get the recommended amount of seven to eight hours of sleep each night. Estimates indicate that sleep deprivation and its associated medical and social costs may exceed $150 billion per year. The primary sleep disorders affecting approximately 50 million Americans include narcolepsy, restless legs/periodic leg movement, insomnia, and sleep apnea. Sleep apnea is defined as the cessation of breathing during sleep and is categorized as obstructive sleep apnea (OSA), central sleep apnea (CSA), and complex sleep apnea (CompSA). OSA is characterized by repetitive pauses in breathing during sleep due to the obstruction and/or collapse of the upper airway (throat), usually accompanied by a reduction in blood oxygen saturation, and often followed by an awakening to breathe (an apnea event). Respiratory effort continues during the episodes of OSA. Multiple episodes of apnea may occur in one night, causing sleep disruption. CSA is a neurological condition causing cessation of all respiratory effort during sleep, usually with corresponding decreases in blood oxygen saturation. In contrast to OSA, where there is respiratory effort from the brain stem but a physical blockage prevents inhalation of oxygen, in CSA the brainstem center controlling breathing shuts down, resulting in no respiratory effort and no breathing. The subject is aroused from sleep by an automatic breathing reflex. Frequent activation of the reflex results in very little sleep for the subject. The neurological mechanism behind CSA is very different from the physical cause of OSA. Although the effects of CSA and OSA are highly similar, effective treatment can differ. CompSA can be thought of as a combination of OSA and CSA. As mentioned before, CompSA is characterized by an emergence of CSA events after CPAP initiation.

Apnea treatment is provided based on the type of apnea, and can be adjusted by re-testing the subject at some later time to determine whether the condition or the symptoms have been alleviated. The most common method of treating OSA is continuous positive airway pressure (CPAP) and positive airway pressure (PAP) devices applied to the subject's airway to force the subject to breathe. When using a simple CPAP device to treat OSA, the air pressure acts as a splint, holding the airway open and reducing or removing the obstruction. The optimal pressure is determined by a sleep technician during a single titration night. The sleep technician manually adjusts the device to deliver a minimum pressure sufficient to force the airway open and reduce the number of apneas. Once the optimal pressure is determined, the device is programmed to consistently provide this pressure, and the patient is sent home.

In order to discover the airway pressure which is most effective for a particular individual, the practice has been for the patient to undergo two sleep studies at an observation facility such as a hospital, clinic or laboratory. The first night is spent observing the patient in sleep and recording selected parameters such as oxygen saturation, chest wall and abdominal movement, air flow, expired carbon dioxide, ECG, EEG, EMG and eye movement. This information can be interpreted to diagnose the nature of the sleeping disorder and confirm the presence or absence of apnea and where present the frequency and duration of apneic episodes and extent and duration of associated oxygen desaturation.

The second night is spent with the patient undergoing nasal CPAP therapy. When apnea is observed the CPAP setting is increased to prevent the apnea. The pressure setting at the end of the sleep period, i.e., the maximum used, is deemed to be the appropriate setting for that patient. For a given patient in a given physical condition there will be found different minimum pressures for various stages of sleep in order to prevent occlusions. Furthermore, these various pressures will, in fact, vary from day to day depending upon the patient's physical condition, for example, nasal congestion, general tiredness, effects of drugs such as alcohol, as well as their sleeping posture. Thus the appropriate pressure found in the laboratory is necessarily the maximum of all these minimum pressures for that particular night and is not necessarily the ideal pressure for all occasions nor for every night. It will generally be higher than necessary for most of the night.

As can be seen there exists the inconvenience and cost of diagnosis which is currently undertaken by overnight observation at a sleep clinic or the like. Hence a simple means whereby a patient's apnea problem can be diagnosed at home without supervision is clearly desirable. There is therefore a need for a system that can quickly and reliably identify a patient's apnea condition without having to undertake a full laboratory based sleep study. There is a further need for a system that can be deployed in a home environment and record a patient's vital signs over the course of a sleep cycle in a manner that then allows reliable identification of a patient's apnea condition without having to undertake a full laboratory based sleep study.

BRIEF SUMMARY OF THE INVENTION

In this regard, the present invention provides a method and system for the analysis of a patient's oximetry data for the detection of sleep-disordered breathing. The system employs an algorithm to reliably detect patient arousals and correlate those with accelerated heart rate and oxygen saturation levels in a manner that detects sleep-disordered breathing via the patient's oximetry data.

Initially a timing channel is formed based on a plethsmography signal using an optical finger sensor. Essentially, based on the change is volume of the finger based on blood flow a high resolution pleth waveform is recorded. It is already well known that the peak to peak timing of this waveform corresponds also to the respiratory rhythm of the individual being tested. Accordingly, based on the pleth waveform, a respiratory wave form is prepared that represents respiration rate. Further first and second derivatives are taken to identify acceleration of the heart rate.

An arousal mask is applied to the signal based on attenuations in the pleth signal. Where there is an attenuation that also corresponds to acceleration in heart rate such masked pleth attenuations are marked as an arousal. Once arousals are identified the time required for changes to propagate from the lungs to the blood gas is subtracted from the onset time of the arousal. As a result if the timing agrees with dropping oxygen saturation or falling arterial pH then the arousal is indicated as a chemoreflex related arousal.

Given this data and algorithm a mask user can be reliably diagnosed as to the state of their sleep disorder without the need for the on-site sleep study and all of the extra diagnostic equipment such as for example, effort belts.

It is therefore an object of the present invention to provide a simple means whereby a patient's apnea problem can be diagnosed at home without supervision. It is a further object of the present invention to provide a system that can quickly and reliably identify a patient's apnea condition without having to undertake a full laboratory based sleep study. It is still a further object of the present invention to provide a system that can be deployed in a home environment and record a patient's vital signs over the course of a sleep cycle in a manner that then allows reliable identification of a patient's apnea condition without having to undertake a full laboratory based sleep study.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention.

DETAILED DESCRIPTION OF THE INVENTION

In the most general embodiment, the present invention provides a method and system for the analysis of a patient's oximetry data for the detection of sleep-disordered breathing. The system employs an algorithm to reliably detect patient arousals and correlate those with accelerated heart rate and oxygen saturation levels in a manner that detects sleep-disordered breathing via the patient's oximetry data.

Figure 1:
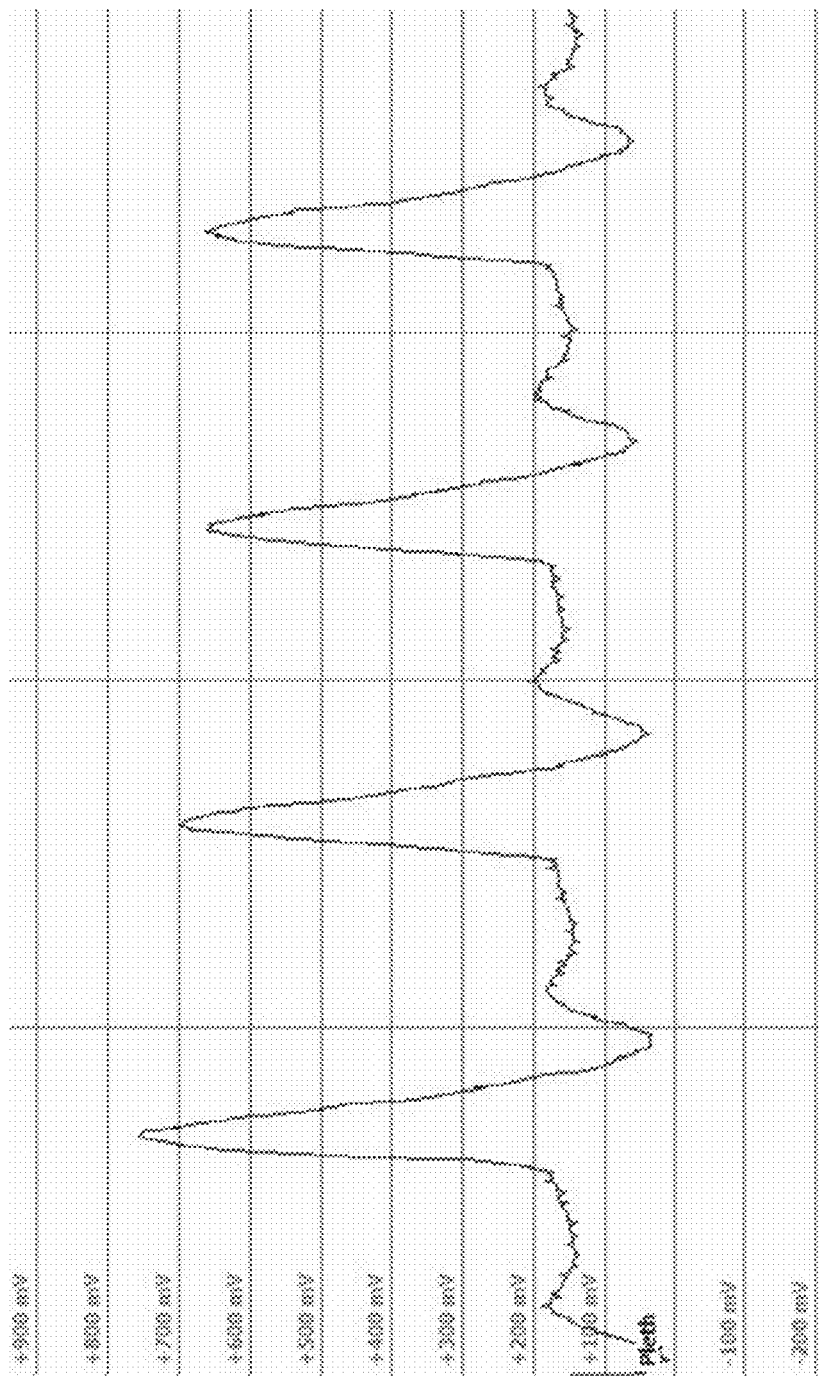
FIG. 1 is a graph of a pleth waveform recorded using a pulse oximeter.

The initial steps in the method and system of the present invention are primarily known. The first step relates to first obtaining a high quality unfiltered pleth signal having a resolution of at least 16-bit/100 Hz as shown at FIG. 1. This pleth signal is formed based on recording a plethsmography signal using an optical finger sensor associated with a pulse oximeter capable of recording a signal at or above the required signal resolution.

Figure 2:
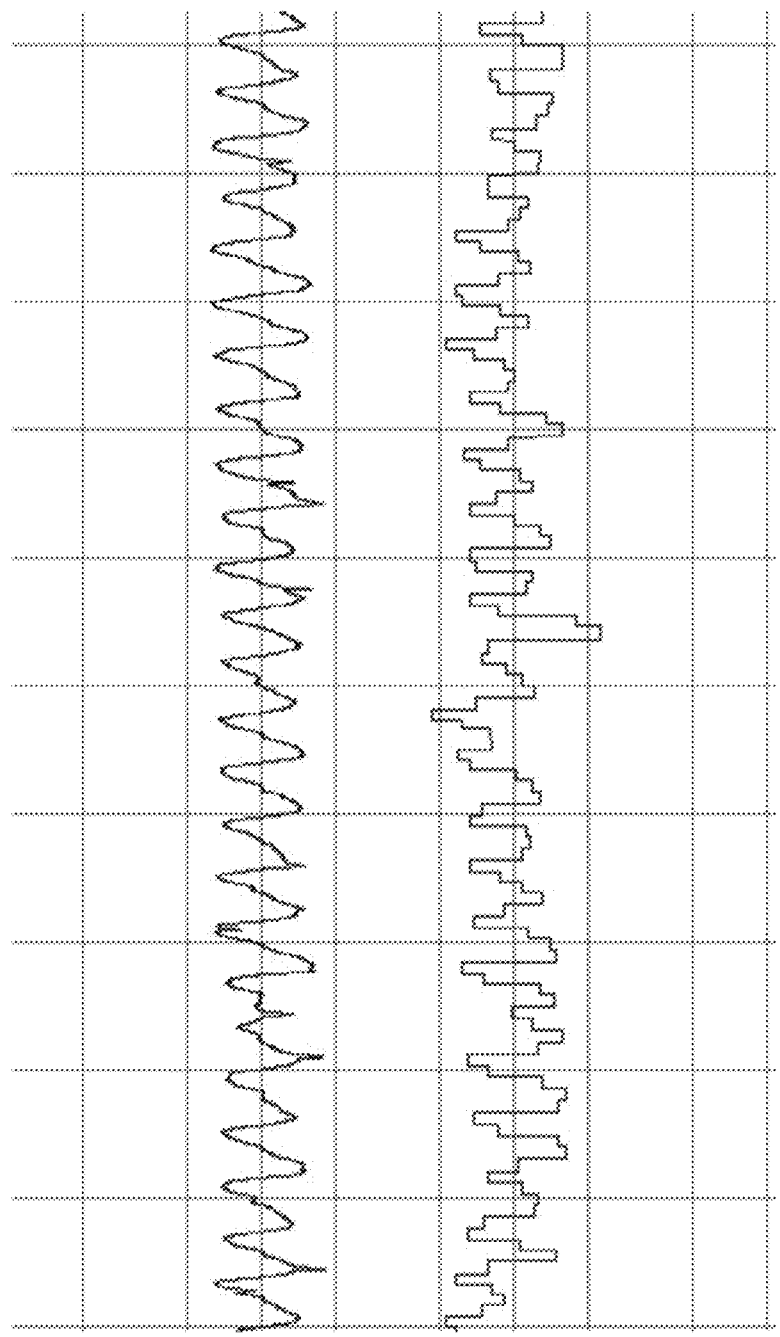
FIG. 2 is a graph depicting the relationship between respiratory effort/rate and changes in heart rate over time.

It is known in the art that, as shown in FIG. 2, a correlation exists as between variations in the heart rate rhythm and the breathing rhythm. In fact it has been shown that a respiratory rhythm channel is embedded in the variations recorded in the heart rate over time. It can be seen that the variations in the heart rate shown in the bottom trace of FIG. 2 accurately reflects the occurrence of breaths taken as shown in the breathing effort shown at the top trace of FIG. 2. Since it is known that a respiratory rate can be predicted based on the heart rate variation, the present invention has determined that the same respiratory timing channel can be derived from the variations in the peak to peak timing of the pleth signal recorded above.

Accordingly, using the peak to peak timing of the pleth signal, a beat to beat channel is prepared that based on the above clearly represents and reflects also the respiratory rhythm. Using the respiratory channel a continuous waveform representing the respiration rate is prepared. Further, channels representing first and second derivatives of the respiration rate are also prepared in order to provide the acceleration and deceleration of the breathing rate as well.

Returning to the pleth signal, any attenuation in the signal is initially identified as an arousal event. This identification of an arousal event is based on the fact that such attenuations are assumed to be related to the release of adrenaline that occurs at the onset of an arousal resulting in peripheral vasoconstriction and therefore attenuation of the pleth signal at the fingertip sensor. The recordation of this data can further provide information demonstrating how big or how long the arousal was. Each of the arousal events is then recorded and the algorithm turns to the next step to assign and record a presumed cause related to the arousal.

To assign a cause related to the arousal events first a time constant must be estimated relating to the time delay between actually taking a breath and the actual registering of the change in blood gasses at the carotid sensors. Based on the delay time constant, the algorithm subtracts the time constant from the timing of the arousal to look back along the respiratory channel for signs of reduction/slowing of breathing rate signal. In a further embodiment, the algorithm may look for changes in amplitude relating to a reduction in breathing effort. If the algorithm finds that the arousal is linked a change in breathing then the arousal is identified as being chemo-reflex related. Other arousals are disregarded.

Further, the arousal is compared to the oxygen saturation reading from the fingertip sensor recorded at the time or slightly after the time of the arousal. If the saturation reading is rising then the arousal can be disregarded. However, if the saturation reading is dropping then this reading can be used to assist in confirming that the arousal is chemo-reflex related.

Figure 3:
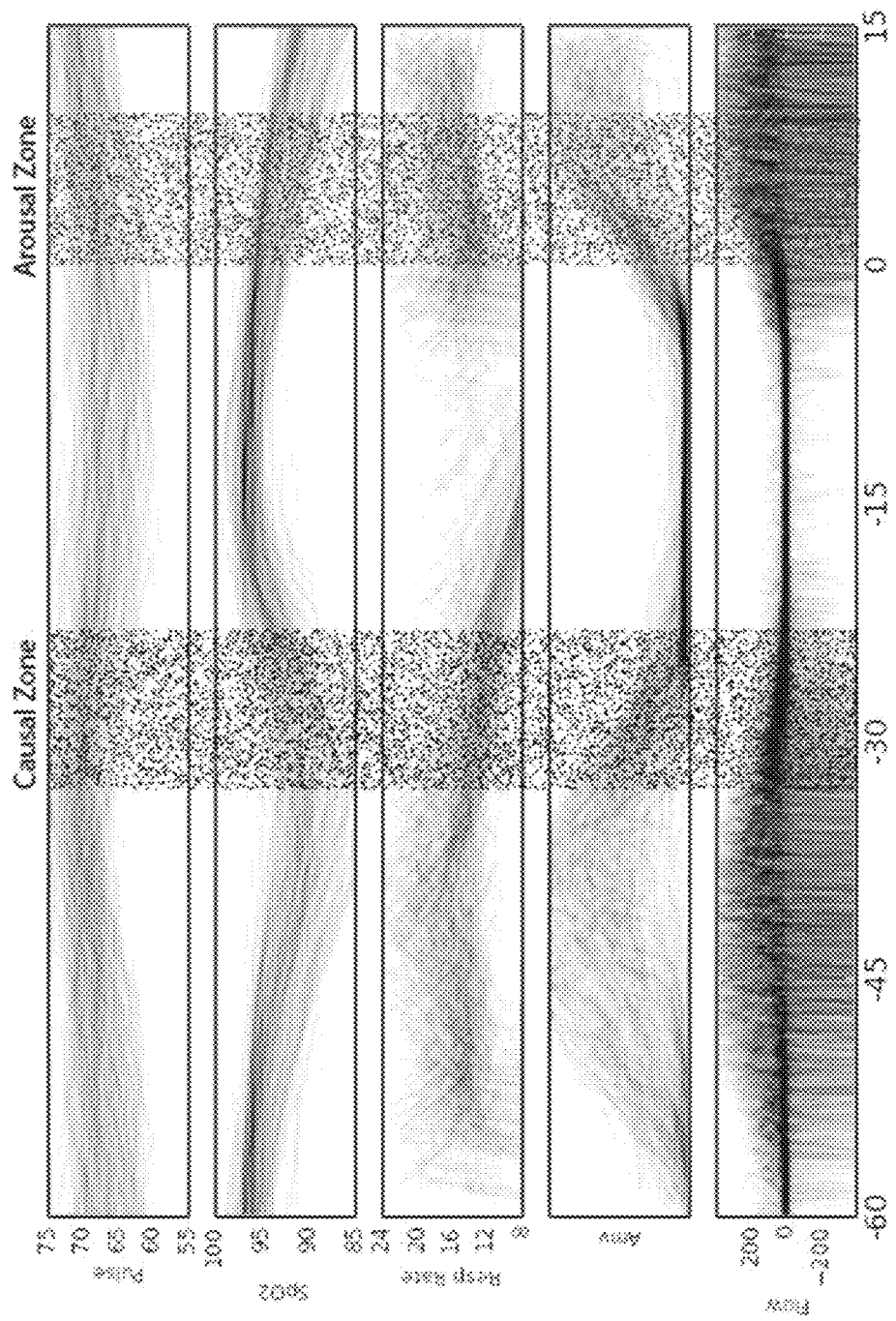
FIG. 3 is a graph showing the overlay of respiratory rate, heart rate and oxygen saturation over time.

The arousals that are identified as being chemo-reflex related are then recorded in an array or an arousal graph. As can be seen in the graph at FIG. 3, a patient with Cheyne Stokes who is having something like 250 separate arousals in a night is graphed. The arousals are all overlaid and each arousal is centered and includes data for sixty seconds before and 15 seconds after each arousal. There are changes in intensity and some outliers, namely that the epoch of decelerating breathing brings about rising $CO_2$, which is sensed by the brain about half a cycle later. A physician could be trained to recognize this pattern at a glance and know that this patient is in big trouble. Since there is a breathing signal encoded in the pleth, with powerful computational means we could do the same with nothing but a pleth-enabled recording oximeter. If a pattern of arousal exists over the course of the monitoring then disordered breathing can be identified.

Given this data and algorithm a mask user can be reliably diagnosed as to the state of their sleep disorder without the need for the on-site sleep study and all of the extra diagnostic equipment such as for example, effort belts.

It can therefore be seen that the present invention provides a simple means whereby a patient's apnea problem can be diagnosed at home without supervision. The system of the present invention can quickly and reliably identify a patient's apnea condition without having to undertake a full laboratory based sleep study. Further the system can be deployed in a home environment and record a patient's vital signs over the course of a sleep cycle in a manner that then allows reliable identification of a patient's apnea condition without having to undertake a full laboratory based sleep study. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A method of diagnosing disordered breathing from a pleth signal:
   recording a pleth signal including a heart rate that undergoes accelerations and decelerations over time;
   using said accelerations and decelerations in heart rate to identify a time based respiratory pattern that is recorded as a continuous waveform;
   identifying attenuations in said pleth signal as arousal events and recording a time of each arousal event;
   subtracting a time constant from the time related to each arousal event to determine a delay time related to each arousal event;
   reviewing said respiratory pattern at each of said delay times to determine if there are changes in said respiratory pattern corresponding to each of said arousal events; and
   recording each of said arousal events that correlate with changes in said respiratory pattern.

2. The method of claim 1, wherein said pleth signal is recorded using a pulse oximeter.

3. The method of claim 1, wherein said changes in said respiratory pattern are a reduction or slowing in respiration rate.

4. The method of claim 1, wherein said changes in said respiratory pattern are changes in respiratory amplitude.

5. The method of claim 1, wherein the time constant is a measured time between actually taking a breath and actually registering a change in blood gasses at carotid sensors.

6. The method of claim 1, further comprising:
   identifying said arousal events that correlate with changes in said respiratory pattern as being chemo-reflex related arousals.

7. The method of claim 6, further comprising:
   reviewing an oxygen saturation reading at or after the time of each arousal, wherein arousals having a rising saturation reading are disregarded and arousals having dropping saturation readings are confirmed as chemo-reflex related.

8. The method of claim 1, further comprising:
   reviewing an oxygen saturation reading at or after the time of each arousal, wherein arousals having a rising saturation reading are disregarded and arousals having dropping saturation readings are identified as chemo-reflex related.

9. The method of claim 1, further comprising:
   generating a graphed array of each of said recorded arousals to identify whether a pattern of arousal exists over time.

10. A method of diagnosing disordered breathing:
    recording a pleth signal including a heart rate that undergoes accelerations and decelerations over time;
    using said accelerations and decelerations in heart rate to identify a time based respiratory pattern that is recorded as a continuous waveform;
    identifying attenuations in said pleth signal as arousal events and recording a time of each arousal event;
    subtracting a time constant that represents a measured time between actually taking a breath and actually registering a change in blood gasses at carotid sensors from the recorded time of each arousal event to determine a delay time related to each arousal event;
    reviewing said respiratory pattern at each of said delay times to determine if there are changes in said respiratory pattern corresponding to each of said arousal events; and
    recording each of said arousal events that correlate with changes in said respiratory pattern.

11. The method of claim 10, wherein said changes in said respiratory pattern are a reduction or slowing in respiration rate.

12. The method of claim 10, wherein said changes in said respiratory pattern are changes in respiratory amplitude.

13. The method of claim 10, further comprising:
    identifying said arousal events that correlate with changes in said respiratory pattern as being chemo-reflex related arousals.

14. The method of claim 13, further comprising:
    reviewing an oxygen saturation reading at or after the time of each arousal, wherein arousals having a rising saturation reading are disregarded and arousals having dropping saturation readings are confirmed as chemo-reflex related.

15. The method of claim 10, further comprising:
    reviewing an oxygen saturation reading at or after the time of each arousal, wherein arousals having a rising saturation reading are disregarded and arousals having dropping saturation readings are identified as chemo-reflex related.

16. The method of claim 10, further comprising:
    generating a graphed array of each of said recorded arousals to identify whether a pattern of arousal exists over time.

* * * * *